United States Patent
Mecikalski

[19]

[11] Patent Number: 6,158,428
[45] Date of Patent: Dec. 12, 2000

[54] INFANT INHALER

[75] Inventor: Mark Mecikalski, Tuscon, Ariz.

[73] Assignee: We Pharmaceuticals Inc., Romona, Calif.

[21] Appl. No.: 09/217,501

[22] Filed: Dec. 21, 1998

[51] Int. Cl.⁷ ............................................. A61M 11/00
[52] U.S. Cl. ............................ 128/200.23; 128/203.12; 128/203.28; 128/203.29
[58] Field of Search .................... 128/200.14, 200.21, 128/200.22, 200.23, 203.12, 203.23, 203.24, 203.25, 203.28, 203.29, 204.28, 205.13, 205.14, 205.17

[56] References Cited

U.S. PATENT DOCUMENTS

| | | | |
|---|---|---|---|
| D. 339,416 | 9/1993 | Maher | D24/110 |
| 3,473,529 | 10/1969 | Wallace | 128/205.13 |
| 4,119,097 | 10/1978 | Spector | 128/203.12 |
| 4,241,740 | 12/1980 | Brown | 128/205.13 |
| 4,484,577 | 11/1984 | Sackner et al. | 128/203.28 |
| 4,790,305 | 12/1988 | Zoltan et al. | 128/200.23 |
| 4,809,692 | 3/1989 | Nowacki et al. | 128/206.24 |
| 4,940,051 | 7/1990 | Lankinen | 128/200.18 |
| 5,040,527 | 8/1991 | Larson et al. | 128/200.23 |
| 5,042,467 | 8/1991 | Foley | 128/200.23 |
| 5,217,006 | 6/1993 | McCulloch | 128/205.13 |
| 5,318,016 | 6/1994 | Mecikalski | 128/200.23 |
| 5,427,089 | 6/1995 | Kramer | 128/200.23 |
| 5,427,091 | 6/1995 | Phillips | 128/205.15 |
| 5,431,154 | 7/1995 | Seigel et al. | 128/200.14 |
| 5,492,115 | 2/1996 | Abramov et al. | 128/205.24 |
| 5,628,305 | 5/1997 | Melker | 128/202.29 |
| 5,701,886 | 12/1997 | Ryatt | 128/203.12 |
| 5,762,063 | 6/1998 | Coates et al. | 128/205.13 |
| 5,842,467 | 12/1998 | Greco | 128/200.23 |
| 5,996,579 | 12/1999 | Coates et al. | 128/205.13 |

FOREIGN PATENT DOCUMENTS

| | | | |
|---|---|---|---|
| 773018 | 11/1934 | France | 128/203.28 |
| 1095470 | 12/1960 | France | 128/205.13 |
| 1544440 | 2/1990 | U.S.S.R. | 128/200.23 |
| 2104394 | 11/1934 | United Kingdom | 128/205.13 |
| 2145335 | 3/1985 | United Kingdom | 128/205.13 |
| 2182249 | 5/1987 | United Kingdom | 128/203.28 |
| 2269754 | 2/1994 | United Kingdom | 128/203.12 |
| 88/02267 | 4/1988 | WIPO | 128/200.23 |
| 88/03419 | 5/1988 | WIPO | 128/200.23 |
| 92/04065 | 3/1992 | WIPO | 128/203.12 |

OTHER PUBLICATIONS

Fuller et al AM Bev Bispir Dis 1990; 141:440–444, Dec. 1990.

Primary Examiner—John G. Weiss
Assistant Examiner—Joseph F. Weiss
Attorney, Agent, or Firm—Mark E. Ogram

[57] ABSTRACT

An infant inhaler in which the aerosol medication is communicated into a flexible bag. Using a mask, during inhalation, the medicated air within the flexible bag is drawn into the infant's lungs; exhalation from the infant is exhausted into the atmosphere. By watching the deflation of the flexible bag, the care-giver is appraised of the progress of the medication's inhalation. The entire assembly is held with one hand allowing the infant to be cradled in the other arm. Refilling of the flexible bag with ambient air is accomplished by inverting the apparatus which causes the valves therein to open and allow ambient air into the flexible bag. Refilling the flexible bag with medication is done using a single hand by pressing the aerosol bottle against the apparatus.

23 Claims, 8 Drawing Sheets

INFANT INHALER

BACKGROUND OF THE INVENTION

This invention relates generally to medical inhalers and more particularly to inhalers adapted for use on an infant.

Medicating the lungs of a patient having respiratory problems is an ancient art. Indigenous natives have long had sweat lodges which used special herbs for the treatment of a variety of ailments.

In more modern times, the same technique is still being used, the introduction of a medication into the lungs of the patient to either treat the lungs themselves or to be absorbed into the blood stream through the lungs. What has changed dramatically is the effectiveness of the medications themselves and the range of ailments that these medications are capable of reaching.

The key to all of these medications remains, how to effectively deliver the proper dosage into the patient's lungs?

To address this problem, a variety of "inhalers" have been developed. These inhalers range in application from the asthma spray applied by the patient herself to inhalers which are used on patients who are unable to administer the inhaler themselves. It is this latter group which is of particular interest as often the physician, nurse, or other care-giver must determine if the proper dosage has been administered and not left within the inhaler.

This problem is accentuated for infants who have extremely low expiration pressures and very small tidal displacements. Since the tidal displacement is so very small, it often requires many respirations for the full dosage to be administered.

To address this problem, a variety of instruments have been developed. One such instrument is described in U.S. Pat. No. 5,427,089, entitled "Valved Auxiliary Device for Use With Aerosol Container" issued to Kraemer on Jun. 27, 1995. This instrument is designed to be placed over the mouth and nose of an infant while the proper dosage is administered into a rigid mixing reservoir. The infant's normal respiration draws in from the mixing reservoir and exhales into the environment.

Unfortunately, this apparatus is particularly difficult to use. Using the instrument of Kraemer requires the use of two hands by the care-giver while the medication is being administered into the mixing reservoir. This means that the infant must either be held by a third party or be in a lying position on a bed or examining table. Either of these methods is difficult to administer.

With rigid mixing reservoirs, each breath entrains ambient air, so that the medication concentration declines with each subsequent breath.

It is clear that there is a need for an improved infant inhaler.

SUMMARY OF THE INVENTION

Within the present invention, an infant inhaler, the aerosol medication is communicated into a flexible bag. The flexible bag is protected by a rigid body so that the care-giver does not inadvertently press upon the flexible bag.

The aerosol medication is applied to the bag using a traditional aerosol applicator which delivers a burst of medication into the air contained within the flexible bag.

Using a mask, during inhalation, the medicated air within the flexible bag is drawn into the infant's lungs; exhalation from the infant is exhausted into the atmosphere. A valve system, located between the flexible bag and the mask, assures that the infant must breathe from the flexible bag and that the exhalation is prevented from entering the flexible bag.

In this manner, each breath from the infant contains the same dosage and is delivered under ambient air pressure. The infant is not required to "suck"; normal breathing is all that is required.

By watching the deflation of the flexible bag, the care-giver is appraised of the progress of the medication's inhalation. When the flexible bag is fully deflated, the care-giver knows that the full dosage has been given, even if it takes only a few breaths or many breaths from the infant.

Administering the medication is also facilitated as the entire assembly is held with one hand of the care-giver, allowing the infant to be cradled in the other arm. Using only a single hand, the care-giver is able to: place and hold the mask over the infant's nose and mouth; administer the proper dosage from the aerosol applicator into the flexible bag; and, monitor the application of the medication as the aerosol bag deflates.

Refilling of the flexible bag with ambient air is accomplished by inverting the apparatus which causes the valves to open and communicate ambient air to the flexible bag. While the "upright" position is the preferred position for refilling the flexible bag, other positions are available so long as the position is not too similar as that taken when using the instrument with an infant.

Refilling the flexible bag with medication is done with one hand by pressing the aerosol bottle against the apparatus using fingers from the supporting hand. The care-giver uses only one hand for the instrument, the other arm and hand is free to cradle the infant during the procedure.

The instrument of this invention provides the care-giver feedback as to whether the infant was inhaling the medication or not. If the flexible bag does not begin collapsing upon placement of the mask on the infant's face (indicating a poor seal between the mask and infant), the mask position is easily adjusted to assure that the infant is breathing from the instrument and is not drawing air from the environment. The flexible bag also allows continuous monitoring of the seal, so adjustments can be made during the entire inhalation period.

In the instrument of this invention, the hand actuating the aerosol canister is close to the mask so that a good seal is more easily obtained. The instrument is ideally designed so that it requires only one hand, leaving the other hand free to support the infant.

Ideally the instrument of this invention is used in a position similar to that used in bottle feeding an infant, which is a very natural and comfortable position.

Further, the design of the instrument allows it to be comfortably shaken with only one hand, without the danger of the aerosol canister falling out, so that multiple doses may be given with only one hand operation. In the preferred embodiment, the securing of the aerosol to the inhaler is accomplished through frictional contact.

To provide the maximum efficiency of aerosol delivery it is important to have a flexible bag which empties as completely as possible with the force generated by infant breathing. In order to do this, and still have a flexible bag durable enough to be cleaned, the ideal flexible bag is made from a thin elastomer film. The preferred embodiment uses a silicone rubber due to its adequate flexibility with a wall thickness providing good durability.

The shape of the flexible bag ideally resembles a child's balloon. This shape has been found to keep the deflation pressure low, even when the chamber was almost totally collapsed. Re-inflation of the flexible bag is assisted if silicone rubber is used. By choosing the proper thickness of the flexible bag, an infant is able to completely deflate the flexible bag, yet, when the bag is exposed to ambient air pressure from within, it will self inflate. The re-inflation of the bag is ideally accomplished when the chamber is hanging freely.

As noted earlier, to protect the flexible bag, it is enclosed within a chamber or sleeve. The ideal chamber is a circumferential clear plastic tube. One end of the tube has an opening in it which allows air to enter and allows the flexible bag to collapse. The other end of the tube is attached to a section which holds the aerosol canister and the valves.

An alternative embodiment uses a chamber/sleeve which is provided with slotted windows to permit the flexible bag to be visible therethrough. In this manner, the care-giver is able to monitor the status of the flexible bag.

The valves in this invention are relatively thick and are ideally attached at only one side, so that the entire dimension of the valve is allowed to flex and respond to pressure changes. This produces a more durable valve, which is still very responsive.

The invention, together with various embodiments thereof, will be more fully explained by the accompanying drawings and the following descriptions.

DRAWINGS IN BRIEF

FIGS. 4A, 4B, 4C, and 4D are cutaway views of the preferred valve system illustrating the valves during rest, inhalation, exhalation, and "re-charge" of the flexible bag respectively.

DRAWINGS IN DETAIL

Figure 1:
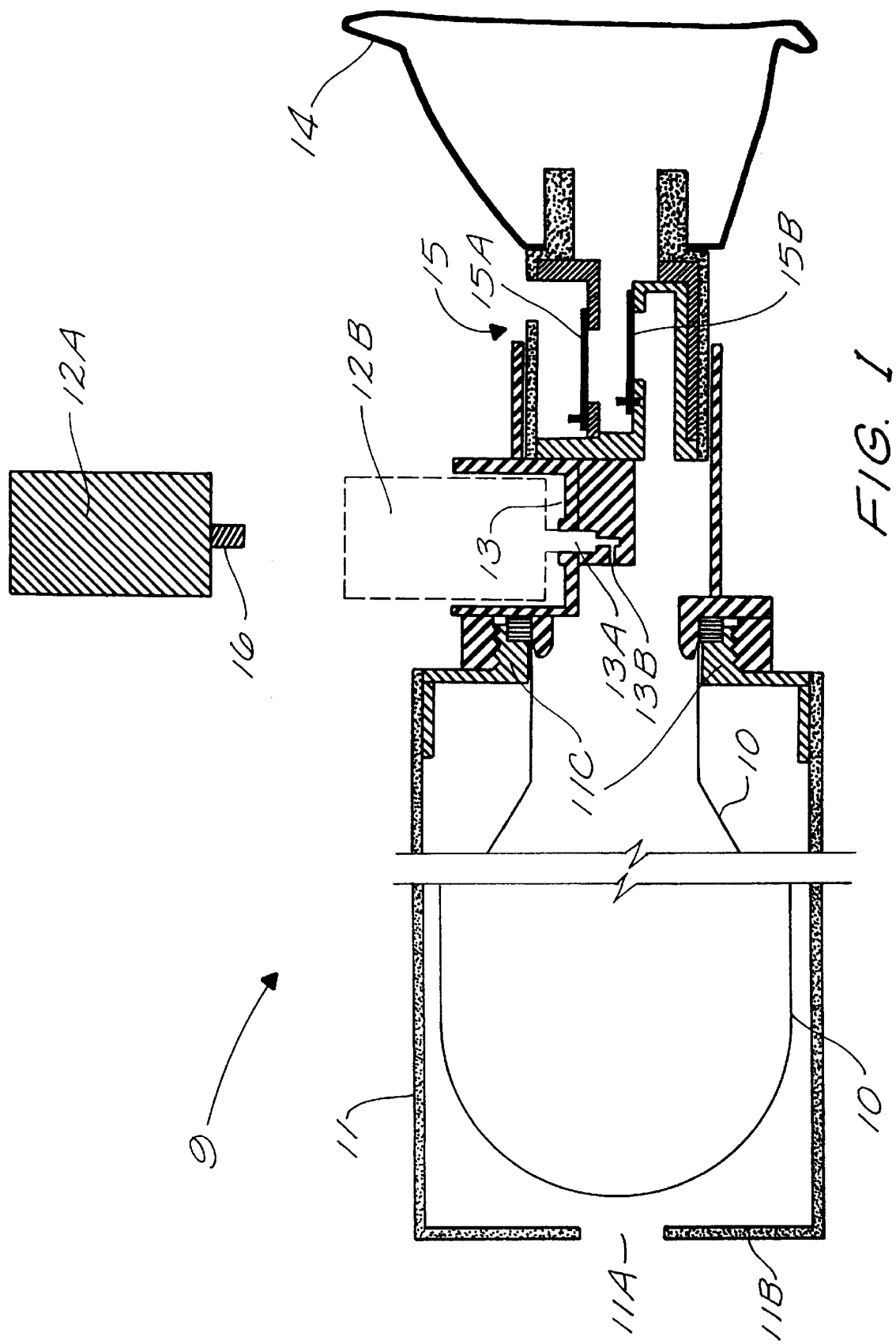
FIG. 1 is a side perspective view of the preferred embodiment of the invention illustrating the entire infant inhaler.

FIG. 1 is a side perspective view of the preferred embodiment of the invention illustrating the entire infant inhaler.

Inhaler 9 is adapted to receive aerosol medication canister 12A into seat 13 where it is held using frictional contact. Once positioned, release 16 of canister 12B fits into receptacle 13A. When pressed downward, release 16 discharges a medicated mist which is communicated via channel 13B into flexible bag 10.

Flexible bag 10 is contained within protective sleeve 11. Opening 11A assures that the exterior of flexible bag 10 is subjected to ambient air pressure; hence, as flexible bag 10 is deflated due to the inhalation of the infant (now shown), the patient's breathing is not stressed but continues under normal conditions.

Monitoring the deflation of flexible bag 10 is facilitated due to the transparent nature of sleeve 11. In some embodiments, sleeve 11 has slot windows to assist in the viewing of flexible bag 10.

In some embodiments, to increase the visibility of flexible bag 10, the material of flexible bag 10 is tinted during manufacture so that the bag has a readily seen color. In other embodiments, the bag is transparent to facilitate viewing the aerosol plume.

Flexible bag 10 is easily changed by un-screwing sleeve 11 via screw-attachment 11C to reveal flexible bag 10.

Base 11B of protective sleeve 11, is flat to allow inhaler 9 to be easily placed upon a table top. Once resting on base 11B, inhaler 9 is vertical which permits flexible bag 10 to re-inflate naturally.

Once the interior of flexible bag 10 has been charged with medication, as outlined above, the medicated air is communicated via valve system 15 to the infant patient. During inhalation, the medicated air from flexible bag 10 is communicated through valve system 15; in this state, valve 15B is opened and valve 15A is closed. During exhalation, the exhale is exhausted when valve 15A opens and valve 15B closes.

In this manner, only medicated air is inhaled, and all of the patient's exhalation is exhausted into the environment and not into flexible bag 10. The medicine/air content of each breath taken by the infant is identical.

Mask 14 is secured to inhaler 9 and is used to provide a tight fit over the infant's nose and mouth. In use, the care-giver is able to monitor the deflation of flexible bag 10 to assure that mask 14 is properly sealed to the face of the patient. If flexible bag 10 is deflating during the breathing of the patient, then a proper seal of mask 14 is obtained; if flexible bag 10 is not deflating, then the care-giver must adjust inhaler 9 (and by extension mask 14) so that a proper seal is obtained. Mask 14 is optionally rotated 180° to permit operation with either hand.

In this manner, an inhalation kit is created which contains an inhaler applicator 9 and an aerosol medication bottle 12A. The applicator 9 is configured to be held with a single hand. The applicator includes: a mask 14 configured to be placed over an infant's nose and mouth; a flexible bag 10 contained within applicator 9; and, a valve system 15 configured to communicate air to mask 14 from the flexible bag 10 during patient inhalation, and to exhaust air from mask 14 during patient exhalation. An aerosol medication bottle 12A is included within the kit and is connectable (12B) to applicator 9 in such way that exhaust from the aerosol medication bottle 12B is communicated into flexible bag 10.

Figure 2A:
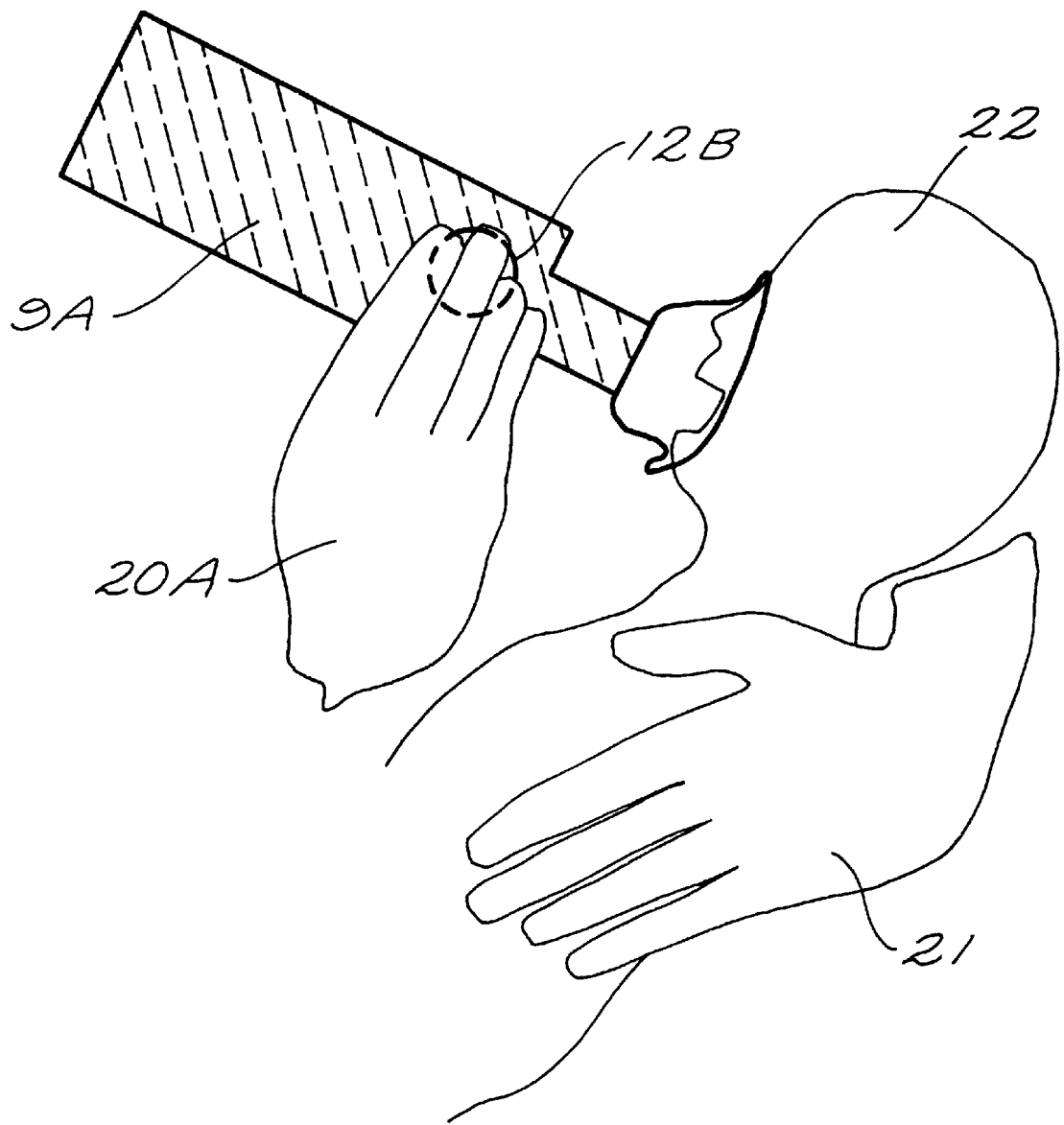
FIGS. 2A and 2B illustrate the use of the inhaler of FIG. 1 in application on an infant patient and during "re-charge" of the flexible bag.
Figure 2B:
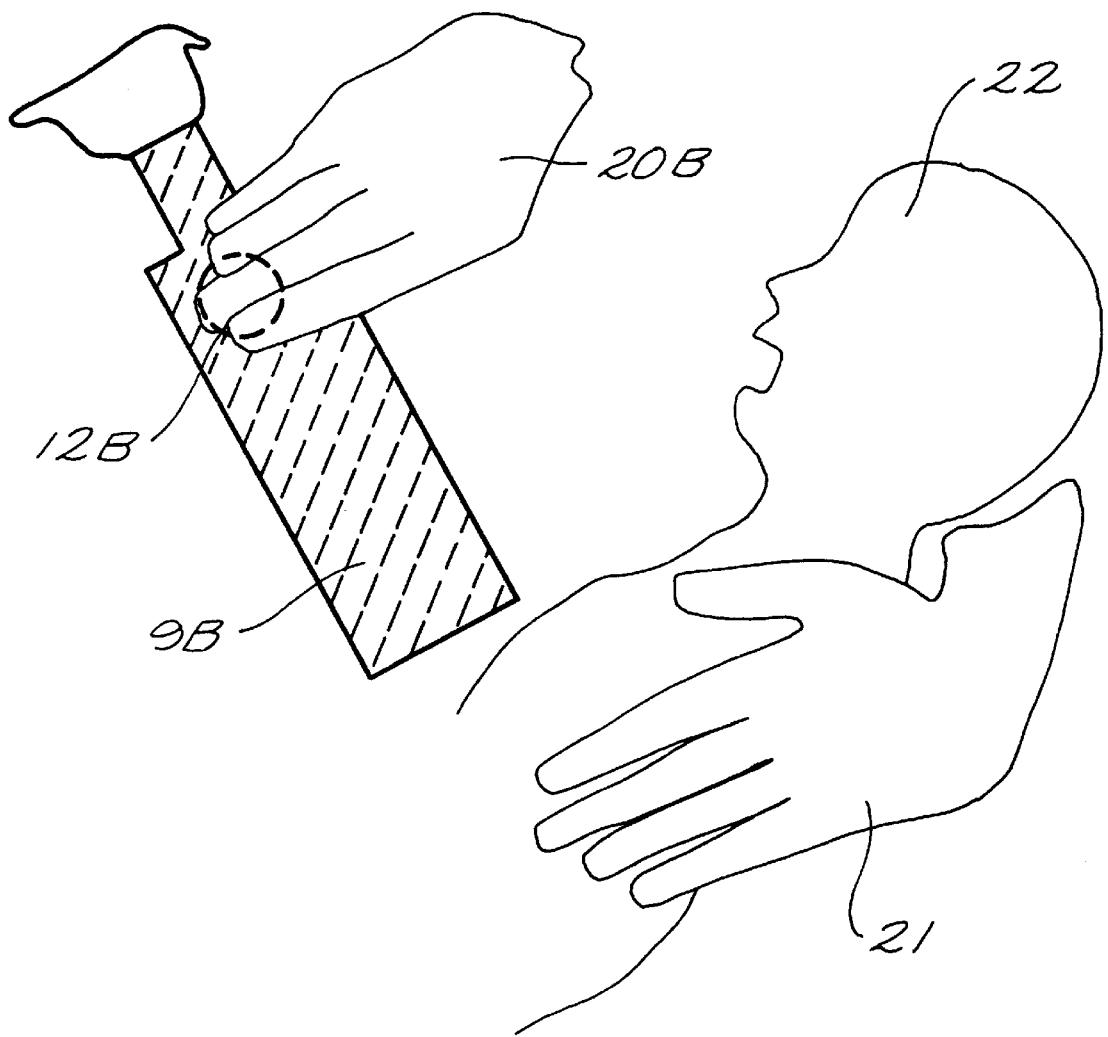

FIGS. 2A and 2B illustrate the use of the inhaler of FIG. 1 in application on an infant patient and during "re-charge" of the flexible bag.

Once the flexible bag has been charged with medication, inhaler 9A is placed over the nose and mouth of infant 22. Due to the arrangement of inhaler 9A, a single hand 20A is used to support and position inhaler 9A while the other hand 21 is freed to support infant 22.

In order to "re-charge" or inflate the flexible bag (not shown), as shown in FIG. 2B, using a single hand 20B, inhaler 9B is placed into a position whereby the valves are opened allowing ambient air to enter the flexible bag.

Canister 12B is positioned on inhaler 9A allowing the user's hand 20A to compresses canister 12B to charge the flexible bag with medication. Further, the entire assembly (including canister 12B) is easily shaken by a single hand 20B to provide a more efficient release of the medication from canister 12B.

Ideally, canister 12B is secured to inhaler 9A through a frictional grip to prevent canister 12B from being dislodged during shaking or use of inhaler 9A. The operator's hand is also holding the canister in place.

Figure 3:
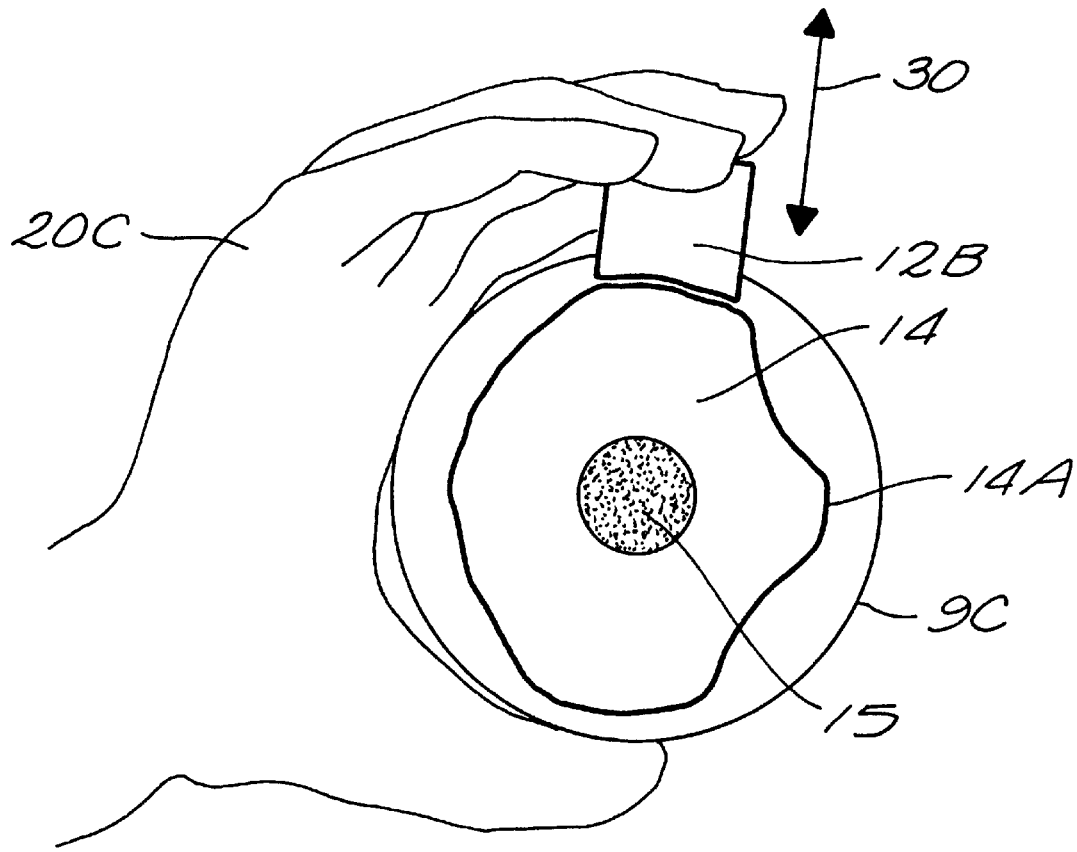
FIG. 3 is a frontal view of the preferred embodiment illustrating the one-hand refilling of the flexible bag with aerosol medication.

FIG. 3 is a frontal view of the preferred embodiment illustrating the one-hand refilling of the flexible bag with aerosol medication.

Using a single hand 20C, the care-giver grasps inhaler 9C and squeezes, as indicated by arrow 30. This pressure causes canister 12B to release its medication into the flexible bag. In application, inhaler 9C, in this illustration, is held in the right hand 20C, with the mask 14 away from the operator.

Note that canister 12B is vertical, as it must be to properly discharge the medication. Inhaler 9C is held in this position while the whole unit is shaken, and then canister 12B is actuated to spray into the flexible bag.

Once the flexible bag is charged, the inhaler is placed on the infant's face. In this embodiment, the nasal portion 14A of mask 14 is positioned at about a right angle to canister 12B. This relationship of canister 12B to mask 14 provides a more comfortable position of the care giver's wrist during treatment.

Since the inhaler is placed onto the infant's face, without requiring the re-positioning of the hand position, inhaler 9C naturally rotates with the arm so that mask 14 is in proper vertical position, and canister 12B is now horizontal.

FIGS. 4A, 4B, 4C, and 4D are cutaway views of the preferred valve system illustrating the valves during rest, inhalation, exhalation, and "re-charge" of the flexible bag respectively.

Figure 4A:
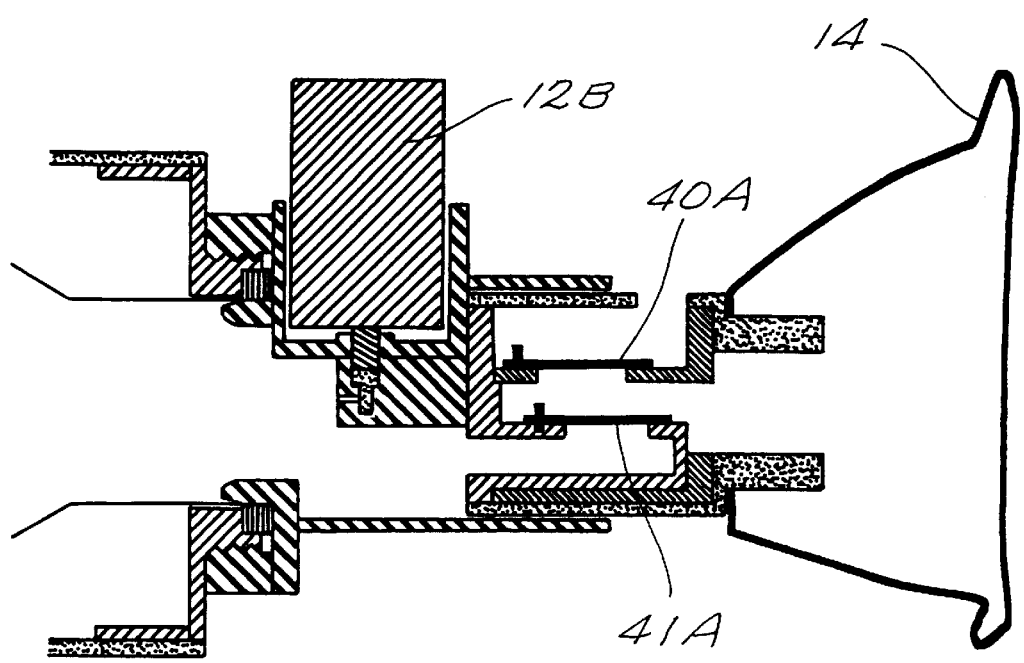

Referring to FIG. 4A, the "relaxed state", in this state valve 40A and 41A are both closed. This is the state where the mask has not been placed over the nose and mouth of the infant or the state between inhalation and exhalation.

Figure 4B:
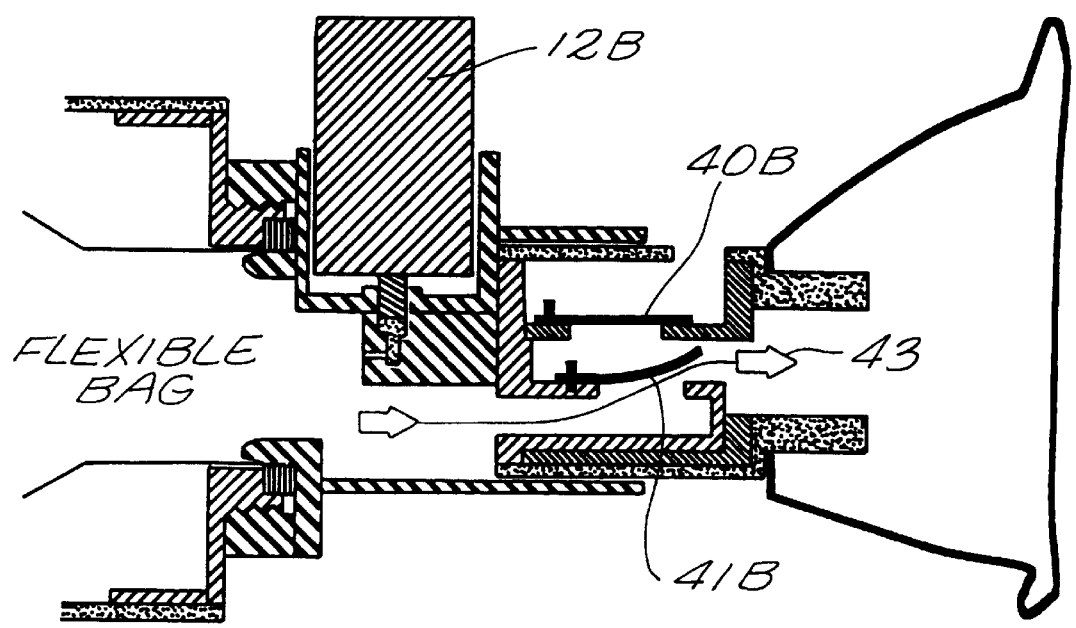

During inhalation, FIG. 4B, valve 40B is closed, while valve 41B opens allowing a flow of medicated air 43 to be communicated from the flexible bag to the lungs of the patient.

Figure 4C:
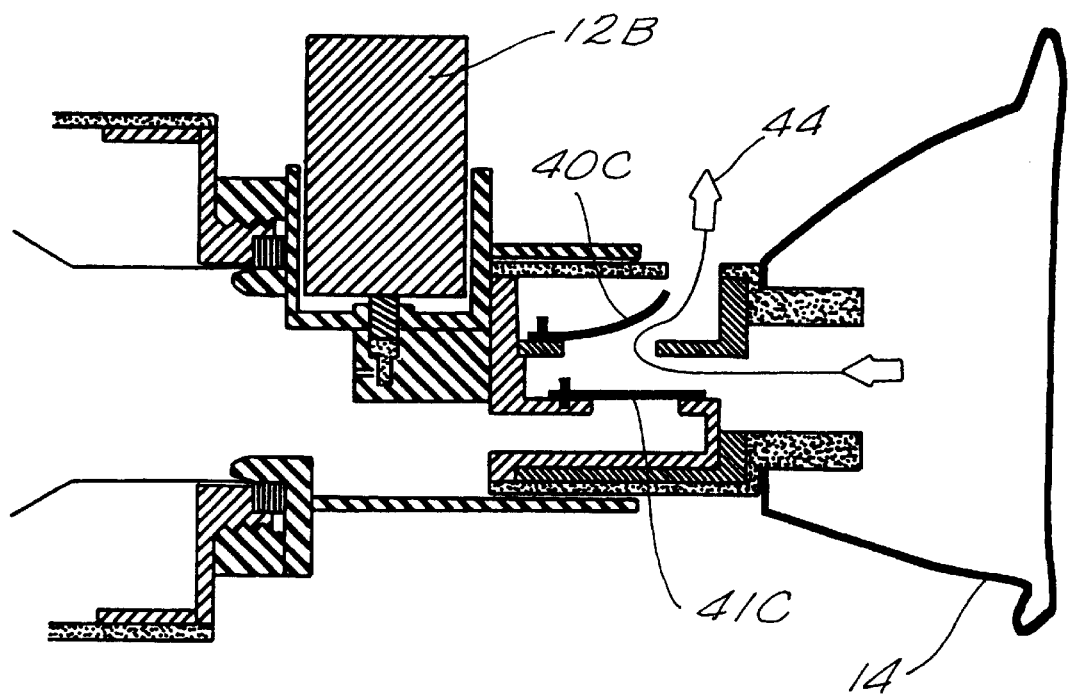

During exhalation, FIG. 4C, valve 41C is closed and valve 40C is opened allowing exhaled air 44 to be exhausted.

Figure 4D:
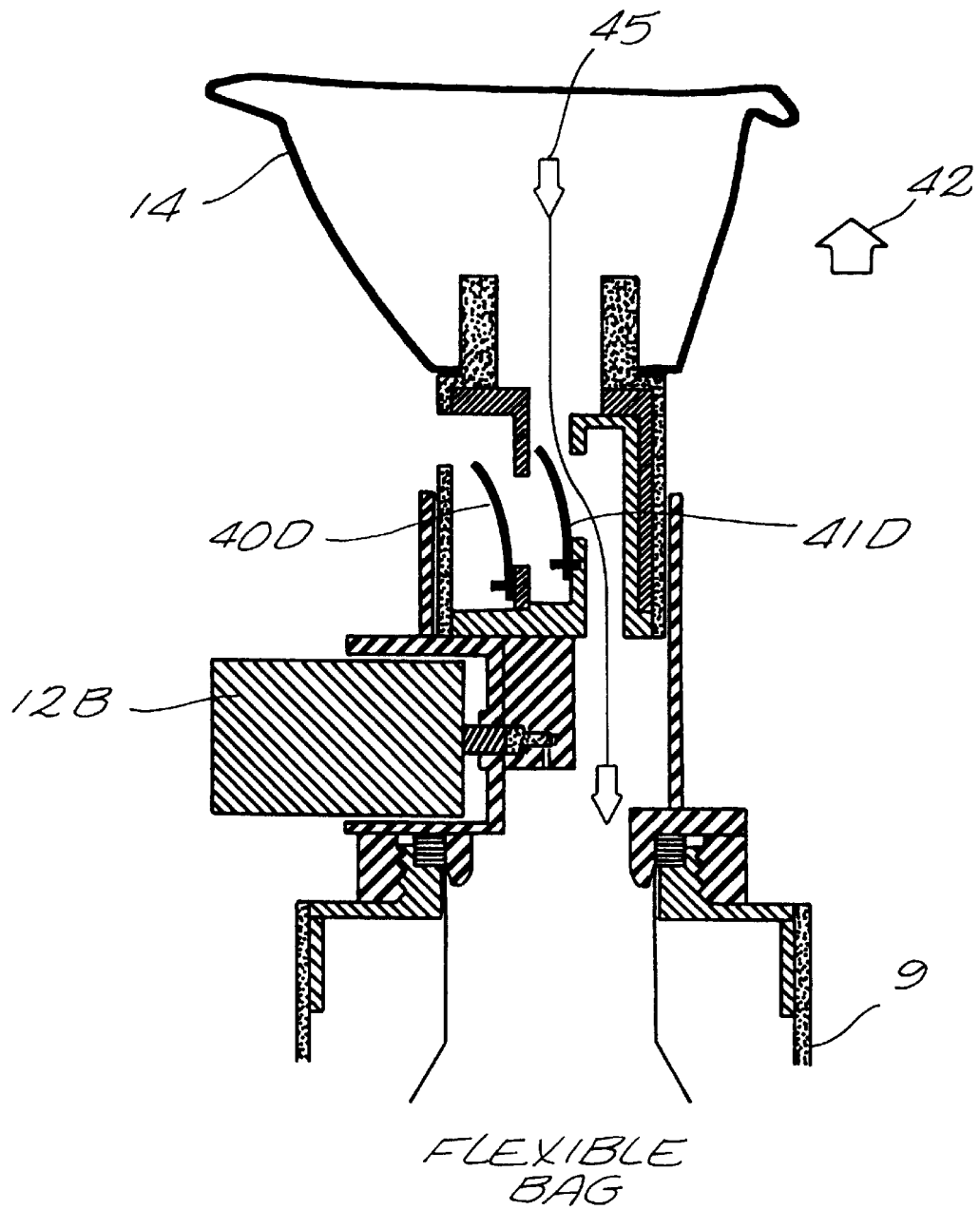

Referring to FIG. 4D, to re-inflate the flexible bag, inhaler 9 is placed in a vertical, or almost vertical position, as indicated by arrow 42. In this position, valve 40D and valve 41D fall open to allow ambient air 45 to pass through to the flexible bag.

It is clear that the present invention creates a highly versatile and effective infant inhaler.

What is claimed is:

1. An infant inhaler comprising:
    a) a mask configured to be placed over an infant's nose and mouth;
    b) a flexible bag;
    c) a rigid body member totally containing said flexible bag, said rigid body secured to said mask;
    d) a valve system contained with said rigid body, said valve system configured to communicate air to said mask from said flexible bag during patient inhalation, and to exhaust air from said mask during patient exhalation; and,
    e) an aerosol medication bottle connectable to said rigid body such that exhaust from said aerosol medication bottle is communicated to said flexible bag.

2. The infant inhaler according to claim 1, wherein said rigid body includes a reservoir containing said flexible bag such that said flexible bag is viewable within said reservoir.

3. The infant inhaler according to claim 2, wherein said flexible bag is colored.

4. The infant inhaler according to claim 2, wherein said flexible bag is substantially transparent.

5. The infant inhaler according to claim 2, wherein said flexible bag, said valve system, and said mask are substantially in a linear relationship.

6. The infant inhaler according to claim 5, wherein said aerosol medication bottle is substantially at right angles to said reservoir.

7. The infant inhaler according to claim 5, wherein said aerosol medication bottle is activatable by pressing said aerosol medication bottle against said rigid body member.

8. The infant inhaler according to claim 7, wherein said rigid body member and said aerosol medication bottle are configured to be grasped with a single average hand.

9. The infant inhaler according to claim 1, wherein said valve system allows ambient air to enter said flexible bag when said rigid body is in a pre-determined position.

10. The infant inhaler according to claim 1,
    a) wherein said reservoir includes a base surface configured to support said infant inhaler when said infant inhaler is placed on a surface; and,
    b) wherein said valve system is in an open condition allowing ambient air to enter said flexible bag when said infant inhaler is supported by said base surface.

11. The infant inhaler according to claim 10, wherein said flexible bag is removable from said rigid body member.

12. An inhalation kit comprising:
    a) a rigid applicator configured to be held with a single hand, said applicator having,
        1) a mask configured to be placed over an infant's nose and mouth,
        2) a flexible bag contained within said applicator, and,
        3) a valve system configured to communicate air to said mask from said flexible bag during patient inhalation, and to exhaust air from said mask during patient exhalation; and,
    b) an aerosol medication bottle connectable to said rigid body such that exhaust from said aerosol medication bottle is communicated into said flexible bag.

13. The inhalation kit according to claim 12, wherein said flexible bag is viewable within said applicator.

14. The inhalation kit according to claim 13, wherein said flexible bag, said valve system, and said mask are substantially in a linear relationship.

15. The inhalation kit according to claim 14, wherein, once connected to said applicator, said aerosol medication bottle is activatable by pressing said aerosol medication bottle against said applicator.

16. The inhalation kit according to claim 15, wherein, once assembled, said applicator and said aerosol medication bottle are configured to be grasped with a single average hand.

17. The inhalation kit according to claim 12, wherein said valve system allows ambient air to enter said flexible bag when said applicator is in a pre-determined position.

18. A medicated aerosol applicator assembly comprising:
    a) a mask configured to be placed over an infant's nose and mouth;
    b) a rigid body member containing a flexible bag;
    c) a valve system connected to said rigid body member and said mask, said valve system configured to communicate air to said mask from said flexible bag during patient inhalation, and to exhaust air from said mask during patient exhalation; and, d) an aerosol medication bottle connectable to said rigid body such that exhaust from said aerosol medication bottle is communicated into said flexible bag.

19. The medicated aerosol applicator assembly according to claim 18, wherein said rigid body, said valve system, and said mask are substantially in a linear relationship.

20. The medicated aerosol applicator assembly according to claim 19, wherein said aerosol medication bottle is substantially at right angles to said rigid body member.

21. The medicated aerosol applicator assembly according to claim 20, wherein said aerosol medication bottle is activatable by pressing said aerosol medication bottle against said rigid body member.

22. The medicated aerosol applicator assembly according to claim 21, wherein said rigid body member and said aerosol medication bottle are configured to be grasped with a single average hand.

23. The medicated aerosol applicator assembly according to claim 18, wherein said valve system allows ambient air to enter said flexible bag when said rigid body is in an upright position.

* * * * *